United States Patent
Ritchie

[19]

[11] Patent Number: 5,819,728
[45] Date of Patent: Oct. 13, 1998

[54] GAS TREATMENT HOOD

[76] Inventor: Scott C. Ritchie, 11057 Morning Creek Dr. South, San Diego, Calif. 92128

[21] Appl. No.: 947,456

[22] Filed: Oct. 7, 1997

[51] Int. Cl.$^6$ .................................................. A62B 17/04
[52] U.S. Cl. ............................... 128/201.23; 128/201.22; 128/201.25
[58] Field of Search ........................ 128/201.22, 201.23, 128/201.25, 201.24

[56] References Cited

U.S. PATENT DOCUMENTS

| | | | |
|---|---|---|---|
| 4,236,514 | 12/1980 | Moretti .............................. | 128/201.23 |
| 4,620,538 | 11/1986 | Koegel et al. ..................... | 128/201.23 |
| 5,226,409 | 7/1993 | Bower et al. ...................... | 128/201.23 |

*Primary Examiner*—John G. Weiss
*Assistant Examiner*—Charles W. Anderson
*Attorney, Agent, or Firm*—John R. Duncan; Frank D. Gilliam

[57] ABSTRACT

A hood assembly placeable over a person's head for treating a person with a gas such as oxygen. Basically the assembly includes a resilient neck ring around a user's neck, a soft, rubbery, tubular neck seal with one end connected to the neck ring and the other configured to fit around the user's neck and a transparent hood fastened to a hood ring that can be sealed against the neck ring. Tubes direct gas into and out the hood through ports through the neck ring. Preferably, the seal that engages the neck is marked with indicia showing a series of varying circumferences, so that the neck seal opening can be trimmed to provide a comfortable and sealing circumference for engaging the user's neck. The assembly is particularly adapted to use in providing oxygen to a patient in a hyperbaric chamber.

20 Claims, 2 Drawing Sheets

GAS TREATMENT HOOD

FIELD OF THE INVENTION

This invention relates to a hood for covering a persons head, the hood having a neck seal and devices for introducing oxygen or other gases into the hood.

BACKGROUND OF THE INVENTION

A wide variety of hoods have been developed for enclosing the head of a person and directing oxygen, clean air or other gases into the hood. Generally the hood is at least partially transparent so that the wearer can see out of the hood and a seal is provided around the wearer's neck to prevent the gas being introduced into the hood from leaking out and/or preventing outside gases from entering the hood. These prior hoods vary greatly in effectiveness and wearer comfort.

Some hoods, such as those described by Bower et al. in U.S. Pat. No. 5,226,409 and Werjefelt in U.S. Pat. No. 4,683,880 are intended for protection from toxic gases in the event of a fire or the like. The hood includes a tubular body, a circular top and an elastic lower panel having a circular opening for slipping over a person's head and sealing against the neck. An inlet for clean air is provided in the top or side of the hood. While effective for short time use in a toxic gas environment, the narrow neck seal and sealing pressure against the neck would be uncomfortable and abrading if used for extended periods. Also, having the inlet at the top or side will tend to pull the hood to the side, possibly disrupting the seal and causing the hood to distort and press against the user's head.

Other hoods or the sort described by Jurris et al. in U.S. Pat. No. 5,133,344 and Brockway et al. in U.S. Pat. No. 4,484,573 have panels that extend down over the user's body, perhaps tucked under a smock, to avoid the neck seal problem. However, without an effective seal the gas being directed into the hood can easily leak out, which is undesirable where the gas is oxygen, an anesthetic gas or other special gas.

Where the gas being introduced into the hood as part of hyperbaric oxygen therapy, it is important that all exhaust gas be collected and piped away, since otherwise the oxygen content in the treatment chamber and/or treatment room will increase, resulting in high risk of fire.

Generally, hyperbaric oxygen therapy is conducted on an intermittent basis with pure oxygen or with gases containing very high percentages of oxygen in a hyperbaric chamber maintained at increased barometric pressure. At these high chamber pressures a patient can tolerate higher doses of oxygen for longer periods than otherwise attainable. Also, this results in a large increase in the partial pressure of oxygen dissolved in the blood. In addition to the oxygen transported by the hemoglobin, the oxygen carried in a dissolved state is greatly increased.

Hyperbaric oxygen therapy has been used in treatment of a number of different conditions, such as treatment of decompression sickness, arterial or venous gas embolism, gas gangrene, carbon monoxide poisoning, in as an aid to the healing of slow or non-healing wounds.

While in some cases a face mask is useful in administering oxygen to a patient in a hyperbaric chamber, the masks are uncomfortable for extended use, may leak oxygen into the chamber and cannot be used with patients with facial injuries, facial medical appliances, etc.

Treatment with oxygen in a hyperbaric chamber may require daily treatment for extended periods. It is important that the treatment apparatus be comfortable and non-injurious. Where a tight elastic neck seal, or a seal having an edge taped to the patients body is used, considerable discomfort, abrasion and tape burns may result from extended treatment.

A treatment hood must sit lightly and be well balanced on the patient's body, since a heavy or off-center weight will tend to cause pain in neck or shoulder muscles with extended use. The hood should be capable of being easily put on and removed by the user or an assistant and comfortable for the user when the user is in a reclining position.

Therefore, there is a continued need for improved hoods for administering selected gases, such as oxygen in hyperbaric oxygen treatment programs, that are comfortable in use and can be used by the user in a reclining position, that prevent leakage of the treatment gas into the atmosphere, that have seals that will not significantly damage or irritate the user's skin, that are light in weight and well balanced and can be easily put on or taken off by the user with little, if any, assistance.

SUMMARY OF THE INVENTION

The above-noted problems, and others, are overcome by the hood assembly of this invention, which basically comprises a neck ring for encircling a user's neck, a tubular resilient neck seal molded into the neck ring releasably secures the neck ring at a first end and configured to fit around a user's neck at the other, and an at least partially transparent hood secured to a hood ring, with the hood ring fastenable to the neck ring in a sealing relationship. The centerline through the neck seal is off-set from the center line through the neck ring.

The second end of the neck seal has indicia indicating neck sizes so that the edge can be trimmed to provide a comfortable sealing fit along the neck of the user. Preferably, the indicia include a series of concentric molded in circles having graduated circumferences. The circles are formed as size indicating lines typically formed by pressing an edge into the neck seal material during manufacture. Strips around the end can be cut away with a sharp pair of scissors or the like to provide an opening circumference corresponding to the neck circumference of a particular user.

Ports are provided through the neck ring for attachment of gas inlet and outlet tubes. Preferably, the ports are on the side of the neck ring that extends to the front of the user do to the centerline off-set between the neck seal and the neck ring, so that the gas tubes will not interfere with the user reclining and will not produce a significant off center pull on the hood or cause hood distortion or leakage.

As fore mentioned, the center line of the neck opening is offset from the center line of the neck ring and the ports located in the front of the hood at maximum space between the neck opening and the neck ring make reclining of the user possible.

BRIEF DESCRIPTION OF THE DRAWING

Details of the invention, and of preferred embodiments thereof, will be further understood upon reference to the drawing, wherein.

DETAILED DESCRIPTION OF PREFERRED EMBODIMENTS

Figure 1:
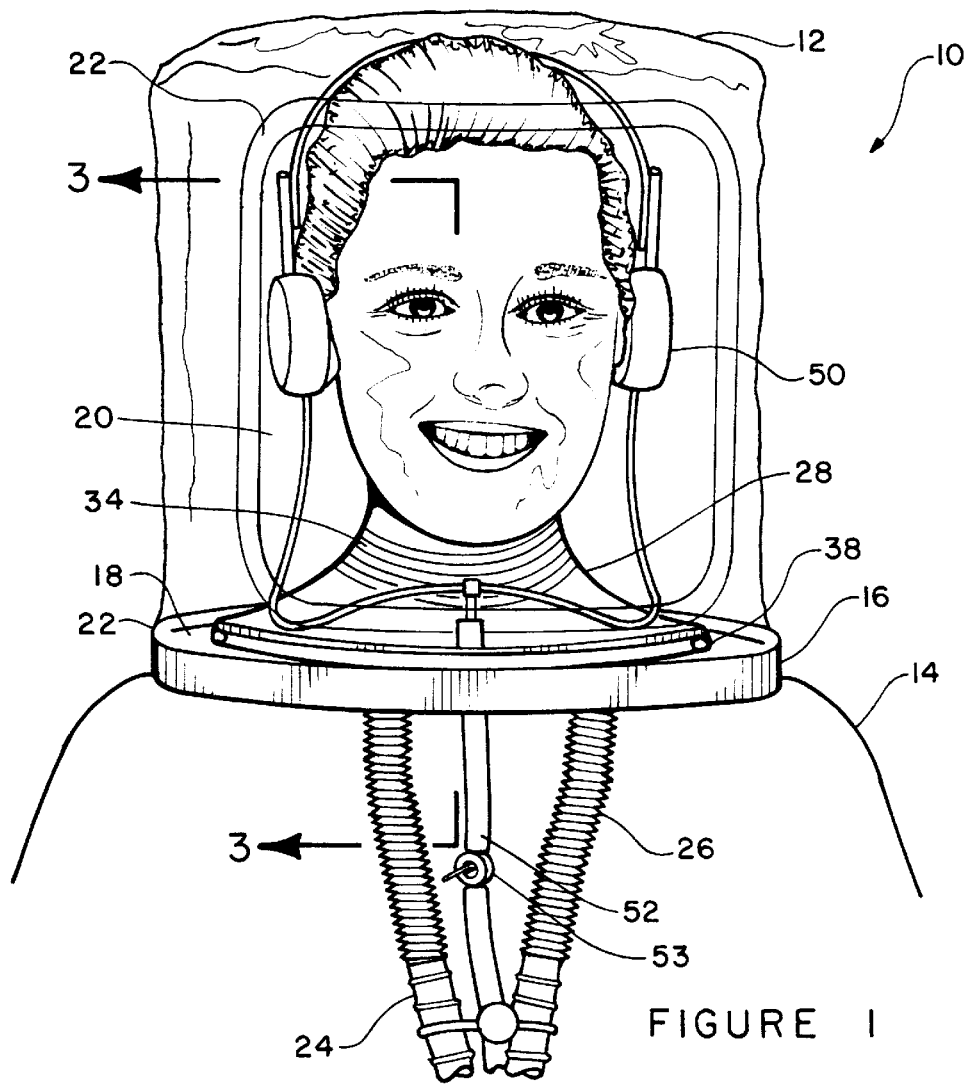
FIG. 1 is a front elevation view of the hood assembly of this invention.

As seen in FIG. 1, the gas treatment hood assembly 10 basically includes a hood 12 that surrounds the head of the user 14 and an assembly of hood ring 16 and neck ring 18 that encircles the neck of user 14.

Hood 12 is at least partially transparent or translucent, with at least the viewing window 20 immediately in front of the eyes of user 14 being transparent and preferably is of optical quality. For optimum flexibility in use and storage combined with best visibility from within hood 12, viewing window is formed from a shape retaining transparent plastic sheet material, typically an optical quality press finished vinyl, acrylic, polycarbonate or similar plastic. Preferably the viewing window has a thickness of from about 0.600 to 1.50 mm. Viewing window 20 is preferably semi-rigid with some flexibility and has high strength and impact resistance.

The balance of hood 12 is preferably formed from a transparent or translucent, very flexible, soft but strong plastic sheet, typically a vinyl or similar plastic, having a thickness of from about 0.125 to 0.550 mm. Viewing window 20 is bonded to the balance of the hood along interface 22 in any suitable manner, such as heat or adhesive bonding.

As detailed below, a gas inlet tube 24 and a gas outlet tube 26 are connected to ports 46 (see drawing FIG. 2) in neck ring 18 to admit a selected gas, such as oxygen, into hood 12 and to evacuate a mixture of the gas and carbon dioxide produced by respiration from hood 12. Any suitable gas may be introduced into the hood. The primary use of the hood assembly is in treatment with pure oxygen or high oxygen concentration gases in a hyperbaric chamber. However, other gases could be used such as air including an anesthetic gas, air with added gases for the treatment of emphysema or other diseases, etc.

The flexibility of hood 12 is such that the viewing window 20 can be folded back against hood ring 16 when not in use. Hood 12 is bonded over the inner or outer circumference of hood ring 16 in any suitable manner, such as by an adhesive, heat sealing, etc.

Figure 3:
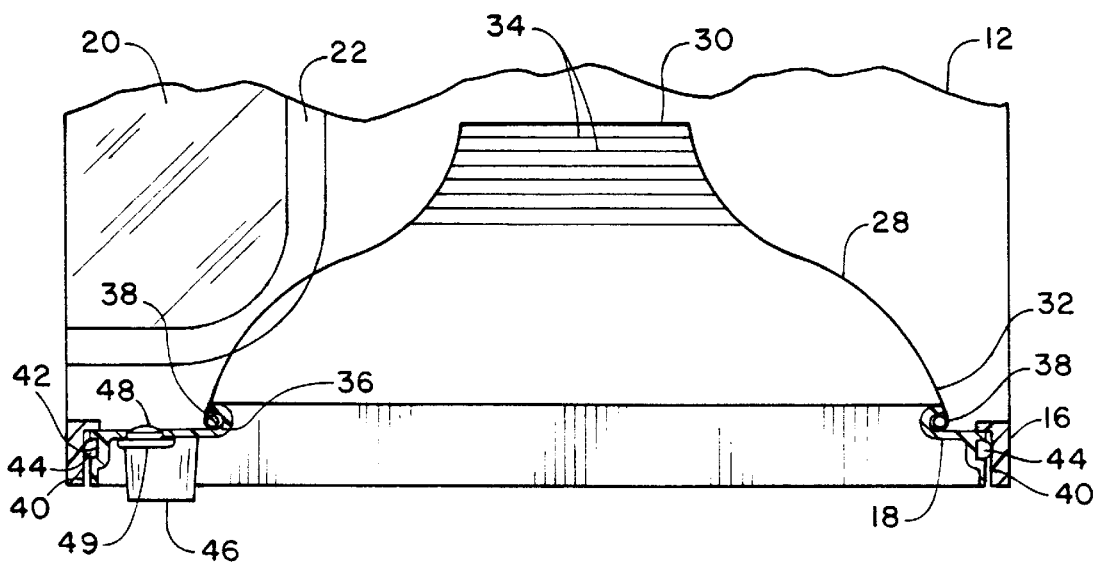
FIG. 3 is an axial section view through the hood assembly, taken on line 3—3 in FIG. 1.
Figure 2:
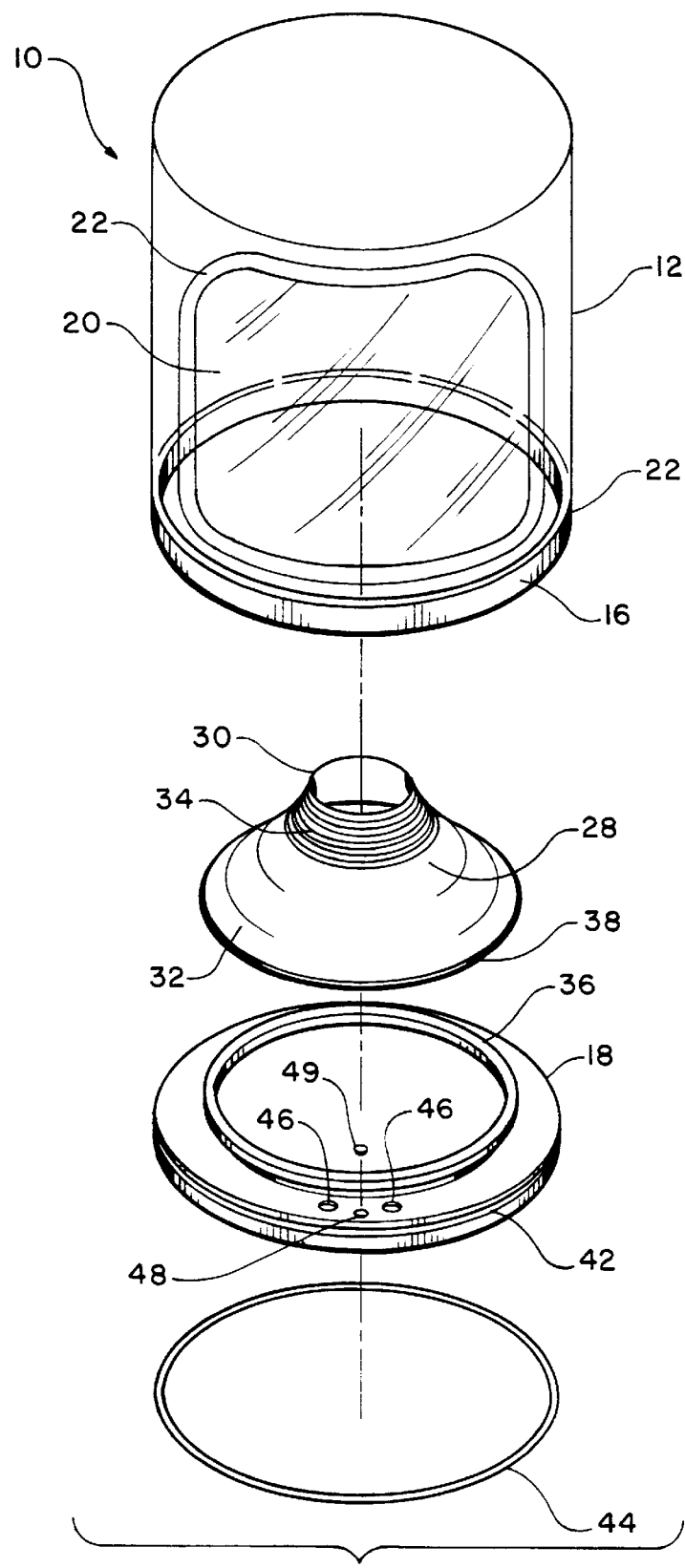
FIG. 2 is an exploded view showing the hood assembly components.

As best seen in FIG. 2 and 3, neck seal has a generally tubular shape, with a large circumference proximal end or edge 32 and a generally frusto-conical distal end 30. Neck seal is formed from any soft, resilient sheet material such as silicone, latex, elastic polymer or the like.

Indicia 34 are provided along distal end 30 to aid in trimming that end to provide a comfortable sealing fit along the user's neck. Preferably, indicia 34 comprise a series of spaced circumferential lines and numbers indicating standard neck sizes. A user's neck size can be easily determined by measuring the neck circumference.

The edge 30 can be simply trimmed with scissors or the like along a selected line. This provides a particularly comfortable sealing fit, which is of considerable importance in preventing skin abrasion or "tape burns" where the hood is used for relatively long periods.

As seen in FIG. 1, the neck seal 28 preferably extends upwardly along the neck skin so that pressure within hood 12 will aid in pressing the ring lightly against the skin to assure a positive seal without excess elastic pressure of the neck seal material against the neck.

Neck seal 28 is releasably secured to neck ring 18 for easy removal for cleaning or replacement to accommodate different users of hood assembly 10. Neck ring 18 has a peripheral outwardly extending recess 36. The proximal end 32 of neck seal 28 is fitted over recess 36 and an O-ring type seal like elastic ring 38 molded into the neck seal is stretched and snapped into recess 36.

The periphery 40 of neck ring 18 has a circumferential, inwardly extending groove 42 in which an elastic sealing ring 44, similar to an O-ring is inserted with the ring extending outwardly slightly above the periphery 40. When neck ring 18 is pressed into hood ring 16, as seen in FIG. 2, sealing ring 44 will both seal against gas leakage from within hood assembly 10 and hold the two rings together. The groove 42 could be formed in either mating surface, the outer surface of neck ring 18 or inner surface of hood ring 16, as desired. If a groove 42 is used in the inner surface of hood ring 16, the circumference of ring 44 will be equal to or slightly greater than the groove circumference to hold ring 44 in place.

Generally, neck ring 18 and neck seal 28 are placed over the user's head, an audio headset or other devices are installed, then hood 12 and hood ring 16 are placed over the user's head and hood and neck rings 18 and 16, respectively are brought together.

At least two ports 46, as seen in FIG. 3, are provided through neck ring 18 to receive ends of inlet and outlet tubes 24 and 26, respectively, as seen in FIG. 1. the center line of the opening at edge 30 of the neck seal is offset from the center line of the hood ring 16 rearly from the viewing window which allows the user to sit or recline without the user's face touching the viewing window and allows the ports 46 to be positioned in the front of the hood adjacent the viewing window. Ports 46 are preferably located in neck ring 18 at a location adjacent to the user's face spaced forwardly therefrom, so that incoming gas will pass along the user's face and viewing window 20, clearing any mist deposits on the viewing window and cooling the user's face and reducing exterior noise. Having ports 46 in neck ring 18 rather than through the top or sides of hood 12 is very advantageous in not pulling the hood down on the user's head and in allowing the user to recline without his or her head encountering or disturbing the gas supply and evacuation hoses. In addition, the position of the ports, as shown and described above, allows the inlet gas to flow over the user's head, down the user's back, towards the front viewing window flushing excess gas out of the exhaust port along with the user's exhaled breath. This feature provides improved gas transfer with minimal $CO_2$ build-up.

At least one additional port 48 is preferably provided between or near ports 46 for insertion of a conventional gas composition measuring device, pneumatic audio headset 50 or the like. When not in use, port 48 is closed by a plug 49.

FIG. 1 shows pneumatic audio tubes 52 with a series volume control valve 53 passing through port 48 to headset 50. Pneumatic tubes for conveying sound to headset 50 are strongly preferred over conventional electromagnetic headsets, since it is very important to keep any electrical devices away from the often very high oxygen content of hood 12.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

I claim:

1. A gas treatment hood assembly, which comprises:
   a neck ring for encircling a user's neck;
   a generally tubular neck seal;
   means at a proximal end portion of said neck seal for securing said proximal end portion to said neck ring;
   indicia along a distal end of said neck seal for indicating neck sizes for trimming of said distal end to provide an opening of predetermined circumference for fitting a predetermined neck circumference;
   an at least partially transparent hood for surrounding a user's head;
   a hood ring secured to said hood;
   means for securing said hood ring to said neck ring in a sealing relationship; and
   means on said neck ring for directing gases into and out of said hood.

2. The gas treatment hood assembly according to claim 1 wherein said distal end of said neck seal has an approximately frusto-conical configuration and said indicia includes a plurality of spaced generally parallel circumferential lines.

3. The gas treatment hood assembly according to claim 2 wherein said parallel circumferential lines are molded into said neck seal so that said neck seal can be cut along predetermined lines.

4. The gas treatment hood assembly according to claim 1 wherein said means for securing said proximal end portion of said said neck ring comprises an outwardly oriented peripheral groove in said neck ring for positioning adjacent to said proximal end portion having a molded in elastic ring having a circumference less than the circumference of said groove for placement over said neck seal proximal end portion and said groove to elastically hold said proximal end portion in said groove.

5. The gas treatment hood assembly according to claim 1 wherein said hood comprises a soft generally transparent material with a highly transparent semi-rigid viewing window across a predetermined area.

6. The gas treatment hood assembly according to claim 1 wherein said means for releasably securing said hood ring to said neck ring comprises an outer peripheral surface on said neck ring, a corresponding hood ring inner surface slidable over said neck ring peripheral surface, a circumferential groove in one of said hood ring inner surface and said neck ring peripheral surface and an elastic ring emplaced in said groove and extending a predetermined distance out of said groove so that said elastic ring seals between said neck ring and hood ring.

7. The gas treatment hood assembly according to claim 1 wherein said means for directing gases into and out of said hood comprises two ports through said neck ring extending from said neck ring opposite to said hood for receiving gas conveying hoses.

8. The gas treatment hood assembly according to claim 1 wherein an auxiliary port and port closure means are provided on said neck ring for passage of auxiliary equipment through said neck ring into said hood.

9. The gas treatment hood assembly according to claim 8 wherein said auxiliary equipment includes a pneumatic audio system including earphones for use by a hood assembly user and having connections extending through said auxiliary port.

10. The gas treatment hood assembly according to claim 1 wherein the center line through said neck seal is off-set from the centerline of said neck ring.

11. A gas treatment hood assembly, which comprises:
    a neck ring for encircling a user's neck;
    an outwardly-oriented groove on said neck ring;
    a tubular seal member having proximal and distal ends;
    said proximal end portion configured to fit over said outwardly-oriented groove;
    means for releasably holding said proximal end portion in said groove;
    said distal end bearing neck size indicia and being trimmable in accordance with said neck size indicia to have a circumference corresponding to a predetermined user neck size;
    a peripheral seal means along said neck ring;
    an at least partially transparent hood for surrounding a users head;
    a hood ring secured to an edge of said hood;
    said hood ring configured to fit said neck ring in a sealing relationship with said peripheral seal means;
    a supply port through said neck ring in communication with said hood; and
    an exhaust port through said neck ring in communication with said hood.

12. The gas treatment hood assembly according to claim 11 wherein said distal end of said neck seal has an approximately frusto-conical configuration and said indicia includes a plurality of spaced generally parallel circumferential lines, said parallel circumferential lines being molded into said neck seal so that said neck seal can be cut along predetermined lines.

13. The gas treatment hood assembly according to claim 11 wherein said means for securing said proximal end portion of said neck seal to said neck ring comprises an outwardly oriented peripheral groove in said neck ring for positioning adjacent to said proximal end portion and an elastic ring molded into said proximal end portion, said elastic ring having a circumference less than the circumference of said groove for placement over said groove and elastically hold said proximal end portion in said groove.

14. The gas treatment hood assembly according to claim 11 wherein said hood comprises a soft approximately transparent material with a highly transparent semi-rigid panel across a predetermined area.

15. The gas treatment hood assembly according to claim 11 wherein said means for releasably securing said hood ring to said neck ring comprises an outer peripheral surface on said neck ring, a corresponding hood ring inner surface slidable over said neck ring peripheral surface, a circumferential groove in one of said hood ring inner surface and said neck ring peripheral surface and an elastic ring emplaced in said groove and extending a predetermined distance out of said groove so that said elastic ring seals between said neck ring and hood ring.

16. The gas treatment hood assembly according to claim 11 wherein an auxiliary port and port closure means are provided on said neck ring for passage of connections between a pneumatic sound generating device 17. The gas treatment hood assembly according to claim 16 wherein said auxiliary equipment includes a pneumatic audio system including earphones for use by a hood assembly user and having connections extending through said auxiliary port.

18. The gas treatment hood assembly according to claim 11 wherein said gas ports are located in said neck ring so that incoming gas will pass between said hood and a user's face whereby the user's face is cooled, misting on said hood adjacent to the user's face will be reduced and outside noise levels will be reduced.

19. The gas treatment hood assembly according to claim 11 wherein the center line through said neck seal is off-set from the centerline of said neck ring.

20. The gas treatment hood assembly according to claim 11 wherein said neck opening allows the inlet gas flow over the user's head, down the user's back, towards the front of the hood pushing excess gas out of said exhaust port along with the user's exhaled breath and minimum $CO_2$ build-up.

* * * * *